United States Patent [19]

Malen et al.

[11] Patent Number: 5,254,590
[45] Date of Patent: Oct. 19, 1993

[54] ACYLAMINOPHENOL COMPOUNDS

[75] Inventors: Charles Malen, Fresnes; Jean-Michel Lacoste, Sevres; Jean-Paul Vilaine, Chatenay-Malabry, all of France; Albert Lenaers, Triel sur Seine, Belgium

[73] Assignee: Adir et Compagnie, Courbevoie, France

[21] Appl. No.: 847,599

[22] Filed: Mar. 5, 1992

[30] Foreign Application Priority Data

Mar. 8, 1991 [FR] France ............................ 91 02800

[51] Int. Cl.$^5$ .................. A01N 37/22; A01N 37/18
[52] U.S. Cl. .................... 514/613; 514/625; 514/627; 554/35; 554/65; 564/170
[58] Field of Search ............... 554/65, 35; 564/170; 514/625, 627, 613

[56] References Cited

U.S. PATENT DOCUMENTS

| | | | |
|---|---|---|---|
| 2,852,540 | 9/1958 | Young et al. | 554/65 |
| 3,479,377 | 11/1969 | Larimer | 554/65 |
| 3,551,462 | 12/1970 | Takashi et al. | 554/35 |
| 3,621,043 | 11/1971 | Seki et al. | 554/35 |
| 3,784,577 | 1/1974 | Fukumaru et al. | 554/35 |
| 4,716,175 | 12/1987 | Hoefle et al. | 514/357 |
| 4,751,026 | 6/1988 | Hoefle et al. | 554/65 |

FOREIGN PATENT DOCUMENTS

| | | |
|---|---|---|
| 22122 | 7/1970 | Japan . |
| 4054119 | 2/1992 | Japan . |
| 1206126 | 9/1970 | United Kingdom . |

Primary Examiner—Jose' G. Dees
Assistant Examiner—Dwayne C. Jones
Attorney, Agent, or Firm—Gordon W. Hueschen

[57] ABSTRACT

The invention relates to the compounds of formula (I):

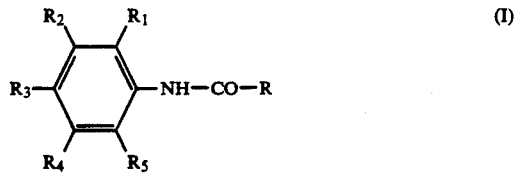

in which
R represents higher alkyl, 1-(higher alkyl)lower cycloalkyl-1-yl or higher alkenyl comprising one or more double bonds, and either
$R_3$ represents hydroxyl,
$R_1$ and $R_2$, which are different, represent hydrogen or lower alkyl,
$R_4$ and $R_5$, which are identical or different, represent lower alkyl or alkoxy, or
$R_1$ and $R_4$ represent hydroxyl and
$R_2$, $R_3$ and $R_5$, which are identical or different, represent lower alkyl or alkoxy, their isomers as well as their salts, and a method for treating an animal or human living body afflicted with dylipidemias or atherosclerosis.

33 Claims, No Drawings

ACYLAMINOPHENOL COMPOUNDS

The subject of the present invention is new acylaminophenol compounds.

Numerous ethylaminophenyl compounds have been described in the literature. Some of them exhibit acyl CoA-cholesterol-acyl transferase—or ACAT—inhibiting properties.

This is the case, more particularly, for the compounds described in the patents EP 242 610, U.S. Pat. No. 4 716 175, EP 344 425, EP 384 320 or U.S. Pat. No. 4 623 662.

The compounds of the present invention are distinct from those described in the prior art not only by virtue of the fact that they are acylaminophenols comprising at least three other substituents on this ring but also by the intensity and the originality of their pharmacological and therapeutic properties.

In fact, these compounds have demonstrated, on the one hand, their acyl CoA-cholesterol-acyl transferase (ACAT)—inhibiting activity and, on the other hand, their ability to protect low density human lipoproteins (LDL) which ensure the transportation of cholesterol, with respect to the oxidative modifications induced by copper.

The ACAT activity which is responsible for the intracellular esterification of free cholesterol is present at the level of intestinal cells (enterocytes) and plays an important role in the intestinal absorption of cholesterol.

It is also found at the level of the smooth vascular muscle cells and of macrophages and is involved in the accumulation of cholesterol esters at the level of these cells which contribute to the formation of atherosclerotic vascular lesions.

The ACAT activity inhibiting power of the compounds of the invention gives them the potential on the one hand to reduce the plasma levels of cholesterol by reducing its intestinal absorption and, on the other hand, to limit the progression of atherosclerotic vascular lesions by inhibiting the accumulation of cholesterol esters in the vascular wall.

The oxidative modifications of the LDLs appear moreover to constitute an important mechanism for the formation and the extension of atherosclerotic vascular lesions. Accordingly, the inhibitory properties of the oxidative modification of LDLs constitute a second therapeutic activity which is quite advantageous.

This dual activity of the compounds of the invention, which has never been shown for the compounds described in the prior art, makes it possible to envisage their use as medication in the treatment of the various types of dyslipidemias and atheroscleroses with their different peripheral, coronary and cerebral vascular localizations.

More specifically, the present invention relates to the compounds of formula (I):

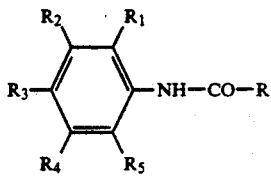

in which:
R represents a linear or branched ($C_8$–$C_{21}$) alkyl group, a linear or branched 1- [($C_8$–$C_{21}$)alkyl](-$C_3$–$C_6$)cycloalk-1-yl group, or a linear or branched ($C_8$–$C_{21}$) alkenyl group comprising one to three double bonds, and either
$R_3$ represents a hydroxyl group, $R_1$ and $R_2$, which are different, represent a hydrogen atom or a linear or branched ($C_1$–$C_6$) alkyl group, $R_4$ and $R_5$, which are identical or different, represent a linear or branched ($C_1$–$C_6$) alkyl group or a linear or branched ($C_1$–$C_6$) alkoxy group, or $R_1$ and $R_4$ represent simultaneously a hydroxyl group, $R_2$, $R_3$ and $R_5$, which are identical or different, represent a linear or branched ($C_1$–$C_6$) alkyl group or a linear or branched ($C_1$–$C_6$) alkoxy group, their enantiomers, diastereoisomers and epimers, their cis/trans isomers as well as their addition salts to a pharmaceutically acceptable base.

Of the pharmaceutically acceptable bases, there may be mentioned, with no limitation being implied, sodium hydroxide or potassium hydroxide and the like.

The present invention also relates to the process for preparing compounds of formula (I), wherein the raw material used is a compound of formula (II)

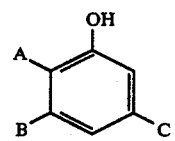

in which the substituents A, B or C, which are identical or different, represent a linear or branched ($C_1$–$C_6$) alkyl group or a linear or branched ($C_1$–$C_6$) alkoxy group
which is reacted:

1 either in the presence of an alkali metal persulfate in the presence of a base,
to give the diphenol of formula (II/a):

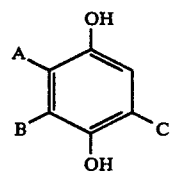

in which the substituents B and C have the same meaning as before,
which is treated with nitric acid in an acetic medium, to give a p-benzoquinone of formula (III):

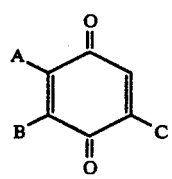

in which the substituents A, B and C have the same meaning as before,
which is then treated
either
in the case where the compounds of formula (I) which it is desired to obtain possess an $R_3$=OH group, in which case A, B and C may be replaced by $R_5$, $R_4$ and $R_2$ respectively, in the presence of hydroxylamine in a hydrochloric medium to give the compound of formula (IV):

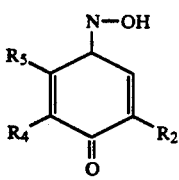
(IV)

in which:

$R_2$, $R_4$ and $R_5$ have the same meaning as in formula (I), or in the case where the compounds of formula (I) which it is desired to obtain possess $R_1=R_4=OH$ groups, in which case A, B and C may be replaced by $R_2$, $R_3$ and $R_5$ respectively, in the presence of hydrochloric acid in an aqueous medium and then of nitric acid to give the compound of formula (V):

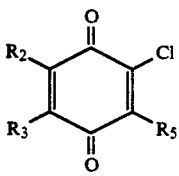
(V)

in which:

$R_2$, $R_3$ and $R_5$ have the same meaning as in formula (I)

which is then reacted in the presence of sodium azide, to give the compound of formula (VI):

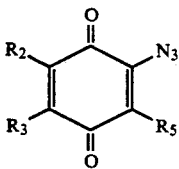
(VI)

in which $R_2$, $R_3$ and $R_5$ have the same meaning as in formula (I), 2 or in the presence of sodium nitrate and using lanthanum trinitrate hexahydrate as catalyst in a hydrochloric medium, to give a mixture of the compounds (VII) and (VIII) which are separated by a conventional separation technique, in the case where the compounds of formula (I) which it is desired to obtain possess:

a $R_1=R_4=OH$ groups, in which case A, B and C may be replaced by $R_2$, $R_3$ and $R_5$ respectively or b an $R_3=OH$ group, in which case A, B and C may be replaced by $R_4$, $R_5$ and $R_1$ respectively

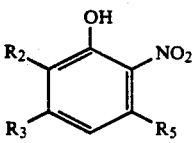
(VII)

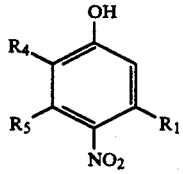
(VIII)

in which $R_2$, $R_3$, $R_4$ and $R_5$ have the same meaning as in the formula (I), which derivative of formula (VII) is reacted with an aqueous solution of an alkali metal persulfate in the presence of a base and which is then treated with concentrated sulfuric acid, to give the compound of formula (IX):

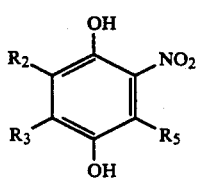
(IX)

in which $R_2$, $R_3$ and $R_5$ have the same meaning as in the formula (I), which derivatives of formulae (IV), (VI), (VIII) and (IX) are subjected to a catalytic hydrogenation, to give the compounds of formulae (X), (XI) and (XII), which are stored under an inert atmosphere:

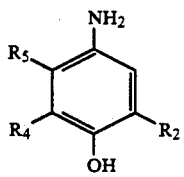
(X)

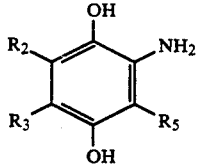
(XI)

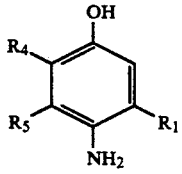
(XII)

in which:

$R_1$, $R_2$, $R_3$, $R_4$ and $R_5$ have the same meaning as in the formula (I), which derivatives of formulae (X), (XI) and (XII) are reacted under an inert atmosphere:

either with a compound of formula (XIII):

$$R-CO-O-CO-O-CH_2-CH_3 \quad (XIII)$$

in which R has the same meaning as in the formula (I), or with a compound of formula (XIV) in the presence of an organic base:

R—CO—Cl     (XIV)

in which R has the same meaning as in the formula (I), to give respectively the compounds of formula (I/a), (I/b) and (I/c) which constitute the set of compounds of formula (I):

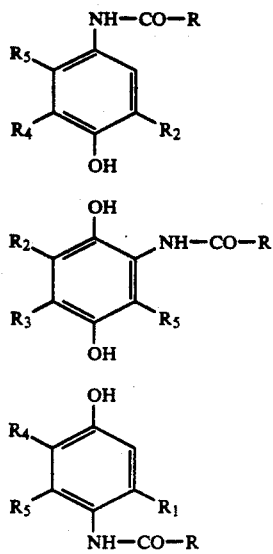

(I/a), (I/b), (I/c)

which compounds of formula (I/a), (I/b) and (I/c) are purified by a conventional purification technique, from which are separated, where appropriate, the optical or cis/trans isomers by conventional separation techniques and which can be converted to their addition salts to a pharmaceutically acceptable base.

The subject of the present invention is also the pharmaceutical compositions containing as active ingredient a compound of general formula (I) or one of its addition salts to a pharmaceutically acceptable base, alone or in combination with one or more inert, nontoxic excipients or vehicles.

Of the pharmaceutical compositions according to the invention, there can be mentioned those which are suitable for oral, rectal, parenteral or nasal administration, simple or sugared tablets, sublingual tablets, sachets, packets, hard gelatin capsules, sublingual preparations, troches, suppositories and the like.

The dosage varies according to the age and the weight of the patient, the nature and the severity of the infection as well as the route of administration. Generally, the unit dosage varies between 50 and 750 mg for a treatment in 1 to 3 takings per 24 hours.

The following examples illustrate the invention but do not imply any limitation.

PREPARATION A

The following preparation gives intermediates which are useful in the process for synthesizing the compounds of the invention.

2,3,5-Trimethyl-6-nitrophenol and 2,3,5-trimethyl-4-nitrophenol

A solution containing 300 mmols of 2,3,5-trimethylphenol in 900 ml of ethyl ether is added dropwise to a vigorously stirred solution containing 300 mmols of sodium nitrate and 3 mmols of lanthanum trinitrate hexahydrate in 300 ml of water and 180 ml of 37% hydrochloric acid while maintaining the temperature at around 6° C. After this addition, the reaction mixture is stirred at 20° C. for 4 hours and then the aqueous phase is removed after settling.

The organic phase is washed with water, dried and evaporated. The residue is chromatographed on a silica column (elution solvent: hexane/ethyl acetate: 85/15) and leaves the two expected products.

2,3,5-Trimethyl-6-nitrophenol

Yield: 38 %.
Melting point: 77°-78° C.

| | Elemental microanalysis: | | |
|---|---|---|---|
| | C % | H % | N % |
| calculated | 59.66 | 6.12 | 7.73 |
| found | 60.07 | 6.34 | 7.77 |

2,3,5-Trimethyl-4-nitrophenol

Yield: 18 %.
Melting point: 80°-81° C.

| | Elemental microanalysis: | | |
|---|---|---|---|
| | C % | H % | N % |
| calculated | 59.66 | 6.12 | 7.73 |
| found | 59.58 | 6.17 | 8.06 |

EXAMPLE 1

4-(9-Octadecenamido)-2,3,5-trimethylphenol, cis isomer

STAGE A: 2,3,5-Trimethyl-4-aminophenol

The expected product is obtained by catalytic hydrogenation of 8 mmols of 2,3,5-trimethyl-4-nitrophenol obtained in Preparation A in solution in 20 ml of anhydrous tetrahydrofuran, at low pressure, in the presence of 50 mg of platinum oxide at 20° C.

STAGE B: 4-(9-Octadecenamido)-2,3,5-trimethylphenol, cis isomer

A suspension of carbethoxy oleate (prepared by reacting at −10° C., in 15 minutes, under a nitrogen atmosphere, 8 mmols of oleic acid with 8 mmols of ethyl chloroformate in the presence of 8 mmols of triethylamine in 20 ml of anhydrous tetrahydrofuran) is added to the preceding solution at 5° C. under a nitrogen atmosphere.

The reaction mixture is stirred for one hour at 20° C. The solvent is then evaporated and the residue is taken up with 50 ml of ethyl acetate. The organic phase is washed with water, dried and evaporated. The expected product is obtained by recrystallization in isopropyl ether.

Yield 72%.

Stage B of this example constitutes Method A of our synthesis process.

EXAMPLE 2

2,3,6-Trimethyl-4-nonanamidophenol

STAGE A: 2,3,5-Trimethylhydroquinone

A solution containing 100 mmols of potassium persulfate in one liter of water is added dropwise with stirring, at 20° C., to a solution containing 100 mmols of 2,3,5-trimethylphenol in 100 ml of a 10% solution of sodium hydroxide. After stirring for 20 hours, the reaction mixture is neutralized with concentrated sulfuric acid and the solid formed is filtered. The remaining aqueous solution is acidified by slowly adding 220 ml of concentrated sulfuric acid, and heated for 30 minutes at 80° C. The oil formed is decanted and extracted with ethyl ether. The expected product is obtained after drying the ether phase, evaporating and recrystallizing in ethyl acetate.

Yield: 93%.
Melting point: 172°-174° C.

STAGE B: 2,3,5-Trimethyl-p-benzoquinone 80 mmols of the product obtained in the preceding stage in solution in 75 ml of acetic acid are treated at 16° C. by dropwise addition of a solution containing 3.8 ml of nitric acid in 15 ml of acetic acid. After stirring for one hour at 20° C., the reaction mixture is poured onto 350 ml of ice cold water. The expected product is obtained in the form of a precipitate which is filtered, washed with ice cold water and dried.

Yield: 95%.
Melting point: 29°-30° C.

| | Elemental microanalysis: | |
|---|---|---|
| | C % | H % |
| calculated | 71.98 | 6.71 |
| found | 71.76 | 6.65 |

STAGE C: 2,3,6-Trimethyl-4-hydroxyimino-p-benzoquinone 33 mmols of the product obtained in the preceding stage and 33 mmols of hydroxylamine hydrochloride are refluxed in 340 ml of 2N hydrochloric acid for 6 hours. The expected product is obtained by filtering the precipitate after cooling, washing with water and then with cyclohexane.

Yield: 85%.
Melting point: 185°-186° C.

| | Elemental microanalysis: | | |
|---|---|---|---|
| | C % | H % | N % |
| calculated | 65.44 | 6.71 | 8.48 |
| found | 65.56 | 6.78 | 8.66 |

STAGE D: 2,3,6-Trimethyl-4-aminophenol

STAGE E: 2,3,6-Trimethyl-4-nonanamidophenol

Stages D and E are identical to Stages A and B of Example 1.

EXAMPLE 3

2,3-Dimethoxy-6-methyl-4-nonanamidophenol

STAGE A: 2,3-Dimethoxy-5-methyl-p-benzoquinone

The expected product is obtained using the same procedure as that described in Stages A and B of Example 2.

STAGE C: 2,3-Dimethoxy-6-methyl-4-hydroxyimino-p-benzoquinone

A mixture containing 88 mmols of the product obtained in the preceding stage, 158 mmols of hydroxylamine hydrochloride and 11 mmols of sodium acetate in 160 ml of methanol is refluxed for 3 hours. After evaporating the methanol, the expected product is obtained at 0° C. by filtering the precipitate formed.

Yield: 68%.
Melting Point: 141°-142° C.

| | Elemental microanalysis: | | |
|---|---|---|---|
| | C % | H % | N % |
| calculated | 54.82 | 5.62 | 7.10 |
| found | 54.45 | 5.57 | 7.21 |

STAGE D: 2,3-dimethoxy-6-methyl-4-aminophenol

STAGE E: 2,6-dimethoxy-6-methyl-4-nonanamidophenol

Stages D and E are identical to Stages A and B of Example 1.

EXAMPLE 4

2,3,6-Trimethyl-4-(2-methylundecanamido)phenol

STAGES A, B and C: 2,3,6-Trimethyl-4-aminophenol

Stages A, B and C are identical to Stages A, B and C described in Example 3.

STAGE D: 2,3,6-Trimethyl-4-(2-methylundecanamido)phenol 8 mmols of triethylamine and 8 mmols of 2-methylundecanoic acid chloride are successively added to the preceding solution. After stirring overnight at 20° C., the solvent is evaporated and the oily residue is dissolved in 75 ml of ethyl ether. The ether phase is washed with water, dried and concentrated under vacuum. The expected product is obtained by recrystallization of the residue in isopropyl ether.

Yield: 64%

Stage D of this example constitutes Method B of our synthesis process.

Examples 5 to 35 as well as 57 and 58 were prepared according to one of the methods A or B described in Examples 1 or 4 and using the 4-aminophenol derivatives prepared according to any one of the processes described in Examples 1 or 2. The methods, A or B, used are specified in Table I, as well as the yields, melting points and results of elemental microanalysis.

EXAMPLE 5

2,3,6-Trimethyl-4-decanamidophenol

EXAMPLE 6

2,3,6-Trimethyl-4-undecanamidophenol

EXAMPLE 7

2,3,6-Trimethyl-4-dodecanamidophenol

EXAMPLE 8

2,3,6-Trimethyl-4-tridecanamidophenol

EXAMPLE 9

2,3,6-Trimethyl-4-tetradecanamidophenol

EXAMPLE 10

2,3,6-Trimethyl-4-hexadecanamidophenol

EXAMPLE 11

2,3,6-Trimethyl-4-octadecanamidophenol

EXAMPLE 12

2,3,6-Trimethyl-4-(2-methyldecanamido)phenol

EXAMPLE 13

2,3,6-Trimethyl-4-(2,2-dimethyldecanamido)phenol

EXAMPLE 14

2,3,6-Trimethyl-4-(2,2-dimethylundecanamido)phenol

EXAMPLE 15

2,3,6-Trimethyl-4-(2,2-dimethyldodecanamido)phenol

EXAMPLE 16

2,3,6-Trimethyl-4-(2,2-dimethyltridecanamido)phenol

EXAMPLE 17

2,3,6-Trimethyl-4-(2,2-dimethyloctadecanamido)-phenol

EXAMPLE 18

2,3,6-Trimethyl-4-(9-octadecenamido)phenol, cis isomer

EXAMPLE 19

2,3,6-Trimethyl-4-(9-octadecenamido)phenol, trans isomer

EXAMPLE 20

2,3,6-Trimethyl-4-(2-methyl-9-octadecenamido)phenol cis isomer

EXAMPLE 21

2,3,6-Trimethyl-4-(9,12-octadecadienamido)phenol cis, cis isomer

EXAMPLE 22

2,3,6-Trimethyl-4-(9,12,15-octadecatrienamido)phenol

EXAMPLE 23

2,3,6-Trimethyl-4-(6,9,12-octadecatrienamido)phenol

EXAMPLE 24

2,3,5-Trimethyl-4-undecanamidophenol

EXAMPLE 25

2,3,5-Trimethyl-4-tetradecanamidophenol

EXAMPLE 26

2,3,5-Trimethyl-4-octadecanamidophenol

EXAMPLE 27

2,3,5-Trimethyl-4-(9,12-octadecadienamido)phenol, cis, cis isomer

EXAMPLE 28

2,3-Dimethoxy-6-methyl-4-decanamidophenol

EXAMPLE 29

2,3-Dimethoxy-6-methyl-4-undecanamidophenol

EXAMPLE 30

2,3-Dimethoxy-6-methyl-4-dodecanamidophenol

EXAMPLE 31

2,3-Dimethoxy-6-methyl-4-tridecanamidophenol

EXAMPLE 32

2,3-Dimethoxy-6-methyl-4-tetradecanamidophenol

EXAMPLE 33

2,3-Dimethoxy-6-methyl-4-hexadecanamidophenol

EXAMPLE 34

2,3-Dimethoxy-6-methyl-4-octadecanamidophenol

EXAMPLE 35

2,3-Dimethoxy-6-methyl-4-(9-octadecenamido)phenol, cis isomer

EXAMPLE 36

3,5,6-Trimethyl-2-nonanamidohydroquinone

STAGE A: 3,5,6-Trimethyl-2-nitrohydroquinone

A solution containing 97 mmols of potassium persulfate in 1100 ml of water is added dropwise with stirring, at 20° C., to a suspension containing 97 mmols of 2,3,5-trimethyl-6-nitrophenol (obtained in Preparation A) in 195 ml of a 10% solution of sodium hydroxide. After stirring for 20 hours, the reaction mixture is neutralized with concentrated sulfuric acid. The solid formed is filtered. The remaining aqueous solution is acidified by adding 200 ml of concentrated sulfuric acid, and heated for 30 minutes at 70° C. The oil formed is decanted and extracted with ethyl ether. The expected product is obtained after drying the ether phase, and evaporating and recrystallizing in an ethyl acetate/hexane mixture.

Yield 85%

Melting point: 105°–106° C.

| | Elemental microanalysis: | | |
|---|---|---|---|
| | C % | H % | N % |
| calculated | 54.82 | 5.62 | 7.10 |
| found | 54.68 | 5.62 | 7.30 |

STAGE B: 2-Amino-3,5,6-trimethylhydroquinone

Catalytic hydrogenation of the product obtained in Stage A is carried out according to the same procedure as that described in Stage A of Example 1.

STAGE C: 3,5,6-Trimethyl-2-nonanamidohydroquinone

The procedure used is Method A described in Stage B of Example 1. The following examples were synthesized following the same procedure as that described in the first two stages of Example 36 and using in Stage C one of the methods A or B as specified in Table 11. Table II contains the yields, melting points and results of elemental microanalysis of the products obtained.

EXAMPLE 37

3,5,6-Trimethyl-2-decanamidohydroquinone

EXAMPLE 38

3,5,6-Trimethyl-2-undecanamidohydroquinone

EXAMPLE 39

3,5,6-Trimethyl-2-dodecanamidohydroquinone

EXAMPLE 40
3,5,6-Trimethyl-2-tridecanamidohydroquinone

EXAMPLE 41
3,5,6-Trimethyl-2-tetradecanamidohydroquinone

EXAMPLE 42
3,5,6-Trimethyl-2-hexadecanamidohydroquinone

EXAMPLE 43
3,5,6-Trimethyl-2-octadecanamidohydroquinone

EXAMPLE 44
3,5,6-Trimethyl-2-(2,2-dimethyloctadecanamido)hydroquinone

EXAMPLE 45
3,5,6-Trimethyl-2-(9-octadecenamido)hydroquinone, cis isomer

EXAMPLE 46
3,5,6-Trimethyl-2-(9-octadecenamido)hydroquinone, trans isomer

EXAMPLE 47
3,5,6-Trimethyl-2-(9,12-octadecadienamido)hydroquinone

EXAMPLE 48
3,5,6-Trimethyl-2-(9,12,15-octadecatrienamido)hydroquinone

EXAMPLE 49
5,6-Dimethoxy-3-methyl-2-dodecanamidohydroquinone

STAGE A: 2,3-Dimethoxy-6-methyl-p-benzoquinone

This stage is identical to Stage A of Example 2.

STAGE B: 2,3-Dimethoxy-5-chloro-6-methyl-p-benzoquinone

A suspension containing 270 mmols of the product obtained in Stage A in 300 ml of 37% hydrochloric acid and 100 ml of water is stirred for three hours at room temperature. This suspension is then poured onto one liter of ice cold water and extracted with ethyl ether. The ether phases are washed with a sodium chloride-saturated aqueous solution until they are neutral, and evaporated. The residue is taken up with one liter of ether cooled to 0° C. and treated with 35 ml of nitric acid for three hours. After stirring for one hour at 10° C., the mixture is poured onto one liter of ice cold water and extracted with ethyl ether. The aqueous phase is washed with 100 ml of a sodium chloride-saturated solution, dried and concentrated. The expected product is obtained after recrystallization of the residue in cyclohexane.

Yield 70%.
Melting point: 66°-68° C.

| | Elemental microanalysis: | | |
|---|---|---|---|
| | C % | H % | N % |
| calculated | 49.90 | 4.19 | 16.37 |
| found | 49.74 | 4.13 | 16.24 |

STAGE C: 2,3-Dimethoxy-5-azido-6-methyl-p-benzoquinone

A solution containing 37 mmols of sodium azide in 30 ml of water is added to a solution containing 18.5 mmols of the product obtained in the preceding stage in 80 ml of 95% ethanol. After stirring for one hour at room temperature, the reaction mixture is poured onto 300 ml of ice cold water and extracted with ether. The ether phases are dried and concentrated. The expected product is obtained by recrystallization of the residue in cyclohexane.

Yield 87%.
Melting point: 48°-50° C.

| | Elemental microanalysis: | | |
|---|---|---|---|
| | C % | H % | N % |
| calculated | 48.42 | 4.04 | 18.83 |
| found | 48.31 | 4.10 | 18.64 |

STAGE D: 5,6-Dimethoxy-3-methyl-2-dodecanamidohydroquinone

The expected product is obtained by carrying out the procedure as in Stage B of Example 1 but replacing the oleic acid with lauric acid.

Yield: 84%.

The following examples were synthesized following the same procedure as that described in the first three stages of Example 48 and using in Stage D one of the methods A or B as specified in Table II. Table II also contains the yields, melting points and results of elemental microanalysis of the products obtained.

EXAMPLE 50
5,6-Dimethoxy-3-methyl-2-decanamidohydroquinone

EXAMPLE 51
5,6-Dimethoxy-3-methyl-2-undecanamidohydroquinone

EXAMPLE 52
5,6-Dimethoxy-3-methyl-2-tridecanamidohydroquinone

EXAMPLE 53
5,6-Dimethoxy-3-methyl-2-tetradecanamidohydroquinone

EXAMPLE 54
5,6-Dimethoxy-3-methyl-2-hexadecanamidohydroquinone

EXAMPLE 55
5,6-Dimethoxy-3-methyl-2-octadecanamidohydroquinone

EXAMPLE 56
5,6-Dimethoxy-3-methyl-2-(9-octadecenamido)hydroquinone, cis isomer

EXAMPLE 57
2,3,6-Trimethyl-4-[(1-decyl-cyclopent-1-yl)carboxamido]phenol

EXAMPLE 58
2,3,6-Trimethyl-4-(2-methyl-9,12-octadecadienamido)phenol, cis, cis isomer

TABLE I

![Structure: phenol with OH, R1, R2, R4, R5 substituents and NH-CO-R group]

| Example No | R₁ | R₂ | R₄ | R₅ | R | Method | Yield (%) | Melting point (°C.) | | Elemental microanalysis | | |
|---|---|---|---|---|---|---|---|---|---|---|---|---|
| | | | | | | | | | | C % | H % | N % |
| 1 | CH₃ | H | CH₃ | CH₃ | CH₃—(CH₂)₇—CH=CH—(CH₂)₇— (cis) | A | 72 | 107-108 | calculated | 78.02 | 10.91 | 3.37 |
| | | | | | | | | | found | 77.99 | 10.71 | 3.40 |
| 2 | H | CH₃ | CH₃ | CH₃ | CH₃—(CH₂)₇— | A | 69 | 143-145 | calculated | 74.18 | 10.03 | 4.81 |
| | | | | | | | | | found | 73.84 | 10.03 | 4.74 |
| 3 | H | CH₃ | CH₃O | CH₃O | CH₃—(CH₂)₇— | A | 63 | 61-62 | calculated | 66.84 | 9.04 | 4.33 |
| | | | | | | | | | found | 66.61 | 8.97 | 4.20 |
| 4 | H | CH₃ | CH₃ | CH₃ | CH₃—(CH₂)₈—CHCH₃— | B | 64 | 149-151 | calculated | 75.63 | 10.58 | 4.20 |
| | | | | | | | | | found | 75.10 | 10.51 | 4.24 |
| 5 | H | CH₃ | CH₃ | CH₃ | CH₃—(CH₂)₈— | A | 77 | 136-138 | calculated | 74.71 | 10.23 | 4.59 |
| | | | | | | | | | found | 74.44 | 10.13 | 4.79 |
| 6 | H | CH₃ | CH₃ | CH₃ | CH₃—(CH₂)₉— | A | 82 | 142-144 | calculated | 75.19 | 10.41 | 4.38 |
| | | | | | | | | | found | 75.28 | 10.31 | 4.32 |
| 7 | H | CH₃ | CH₃ | CH₃ | CH₃—(CH₂)₁₀— | A | 80 | 137-140 | calculated | 75.63 | 10.58 | 4.20 |
| | | | | | | | | | found | 75.51 | 10.95 | 4.23 |
| 8 | H | CH₃ | CH₃ | CH₃ | CH₃—(CH₂)₁₁— | A | 80 | 140-141 | calculated | 76.03 | 10.73 | 4.03 |
| | | | | | | | | | found | 76.12 | 10.64 | 4.05 |
| 9 | H | CH₃ | CH₃ | CH₃ | CH₃—(CH₂)₁₂— | A | 77 | 142-144 | calculated | 76.40 | 10.87 | 3.87 |
| | | | | | | | | | found | 76.05 | 10.97 | 4.13 |
| 10 | H | CH₃ | CH₃ | CH₃ | CH₃—(CH₂)₁₄— | A | 79 | 135-138 | calculated | 77.07 | 11.12 | 3.59 |
| | | | | | | | | | found | 76.85 | 10.97 | 3.51 |
| 11 | H | CH₃ | CH₃ | CH₃ | CH₃—(CH₂)₁₆— | A | 80 | 138-140 | calculated | 77.64 | 11.34 | 3.35 |
| | | | | | | | | | found | 77.31 | 11.40 | 3.33 |
| 12 | H | CH₃ | CH₃ | CH₃ | CH₃—(CH₂)₇—CHCH₃— | B | 68 | 148-150 | calculated | 75.19 | 10.41 | 4.38 |
| | | | | | | | | | found | 74.97 | 10.40 | 4.71 |
| 13 | H | CH₃ | CH₃ | CH₃ | CH₃—(CH₂)₇—C(CH₃)₂— | B | 58 | 68-71 | calculated | 75.63 | 10.58 | 4.20 |
| | | | | | | | | | found | 75.63 | 10.49 | 4.30 |
| 14 | H | CH₃ | CH₃ | CH₃ | CH₃—(CH₂)₈—C(CH₃)₂— | B | 63 | 87-89 | calculated | 76.03 | 10.73 | 4.03 |
| | | | | | | | | | found | 75.67 | 10.34 | 4.50 |
| 15 | H | CH₃ | CH₃ | CH₃ | CH₃—(CH₂)₉—C(CH₃)₂— | B | 60 | 75-76 | calculated | 76.40 | 10.87 | 3.87 |
| | | | | | | | | | found | 76.30 | 10.77 | 4.11 |
| 16 | H | CH₃ | CH₃ | CH₃ | CH₃—(CH₂)₁₀—C(CH₃)₂— | B | 58 | 80-82 | calculated | 76.75 | 11.00 | 3.73 |
| | | | | | | | | | found | 76.55 | 11.40 | 4.00 |
| 17 | H | CH₃ | CH₃ | CH₃ | CH₃—(CH₂)₁₅—C(CH₃)₂— | A | 64 | 79-81 | calculated | 78.15 | 11.53 | 3.14 |
| | | | | | | | | | found | 78.41 | 11.52 | 3.02 |
| 18 | H | CH₃ | CH₃ | CH₃ | CH₃—(CH₂)₇—CH=CH(CH₂)₇ (cis) | A | 57 | 125-127 | calculated | 78.02 | 10.91 | 3.37 |
| | | | | | | | | | found | 77.97 | 10.99 | 3.64 |
| 19 | H | CH₃ | CH₃ | CH₃ | CH₃—(CH₂)₇—CH=CH—(CH₂)₇— (trans) | A | 59 | 127-129 | calculated | 78.02 | 10.91 | 3.37 |
| | | | | | | | | | found | 78.15 | 10.94 | 3.31 |
| 20 | H | CH₃ | CH₃ | CH₃ | CH₃—(CH₂)₅—CH=CH—(CH₂)₆—CH(CH₃)— (cis) | B | 55 | 125-127 | calculated | 78.27 | 11.03 | 3.26 |
| | | | | | | | | | found | 78.04 | 10.95 | 3.20 |
| 21 | H | CH₃ | CH₃ | CH₃ | CH₃—(CH₂)₃—(CH₂)₂—CH=CH—(CH₂)₇— (cis, cis) | A | 68 | 130-132 | calculated | 78.40 | 10.48 | 3.39 |
| | | | | | | | | | found | 78.11 | 10.45 | 3.67 |

TABLE I-continued

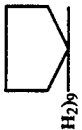

| Example No | R₁ | R₂ | R₄ | R₅ | R | Method | Yield (%) | Melting point (°C.) | Elemental microanalysis | C % | H % | N % |
|---|---|---|---|---|---|---|---|---|---|---|---|---|
| 22 | H | CH₃ | CH₃ | CH₃ | CH₃—(CH₂—CH=CH)₃—(CH₂)₇— | A | 66 | 117–118 | calculated | 78.78 | 10.04 | 3.40 |
|  |  |  |  |  |  |  |  |  | found | 78.91 | 10.23 | 3.55 |
| 23 | H | CH₃ | CH₃ | CH₃ | CH₃—(CH₂)₃—(CH₂—CH=CH)₃—(CH₂)₄— | A | 71 | 106–109 | calculated | 78.78 | 10.04 | 3.40 |
|  |  |  |  |  |  |  |  |  | found | 77.93 | 9.88 | 3.91 |
| 24 | CH₃ | H | CH₃ | CH₃ | CH₃—(CH₂)₉— | A | 67 | 118–120 | calculated | 75.19 | 10.49 | 4.38 |
|  |  |  |  |  |  |  |  |  | found | 75.10 | 10.42 | 4.56 |
| 25 | CH₃ | H | CH₃ | CH₃ | CH₃—(CH₂)₁₂— | A | 74 | 122–124 | calculated | 76.40 | 10.87 | 3.87 |
|  |  |  |  |  |  |  |  |  | found | 76.39 | 10.97 | 3.77 |
| 26 | CH₃ | H | CH₃ | CH₃ | CH₃—(CH₂)₁₆— | A | 72 | 123–125 | calculated | 77.64 | 11.34 | 3.35 |
|  |  |  |  |  |  |  |  |  | found | 77.68 | 11.52 | 3.40 |
| 27 | CH₃ | H | CH₃ | CH₃ | CH₃—(CH₂)₃—(CH₂—CH=CH)₂—(CH₂)₇— (cis, cis) | A | 59 | 102–104 | calculated | 78.40 | 10.48 | 3.39 |
|  |  |  |  |  |  |  |  |  | found | 77.81 | 10.42 | 3.29 |
| 28 | H | CH₃ | CH₃O | CH₃O | CH₃—(CH₂)₈— | A | 64 | 72–73 | calculated | 67.63 | 9.26 | 4.15 |
|  |  |  |  |  |  |  |  |  | found | 67.27 | 9.24 | 4.11 |
| 29 | H | CH₃ | CH₃O | CH₃O | CH₃—(CH₂)₉— | A | 68 | 73–75 | calculated | 68.34 | 9.46 | 3.98 |
|  |  |  |  |  |  |  |  |  | found | 68.30 | 9.37 | 4.13 |
| 30 | H | CH₃ | CH₃O | CH₃O | CH₃—(CH₂)₁₀— | A | 68 | 82–83 | calculated | 69.01 | 9.65 | 3.83 |
|  |  |  |  |  |  |  |  |  | found | 68.65 | 9.65 | 3.91 |
| 31 | H | CH₃ | CH₃O | CH₃O | CH₃—(CH₂)₁₁— | A | 65 | 76–78 | calculated | 69.62 | 9.83 | 3.69 |
|  |  |  |  |  |  |  |  |  | found | 69.41 | 9.83 | 3.87 |
| 32 | H | CH₃ | CH₃O | CH₃O | CH₃—(CH₂)₁₂— | A | 62 | 87–90 | calculated | 70.19 | 9.99 | 3.56 |
|  |  |  |  |  |  |  |  |  | found | 69.45 | 9.84 | 3.77 |
| 33 | H | CH₃ | CH₃O | CH₃O | CH₃—(CH₂)₁₄— | A | 69 | 93–95 | calculated | 71.22 | 10.28 | 3.32 |
|  |  |  |  |  |  |  |  |  | found | 70.87 | 10.06 | 3.35 |
| 34 | H | CH₃ | CH₃O | CH₃O | CH₃—(CH₂)₁₆— | A | 75 | 97–98 | calculated | 72.12 | 10.54 | 3.11 |
|  |  |  |  |  |  |  |  |  | found | 71.78 | 10.53 | 3.14 |
| 35 | H | CH₃ | CH₃O | CH₃O | CH₃—(CH₂)₇—CH=CH—(CH₂)₇— (cis) | A | 78 | 54–56 | calculated | 72.44 | 10.13 | 3.13 |
|  |  |  |  |  |  |  |  |  | found | 72.28 | 9.95 | 3.21 |
| 57 | H | CH₃ | CH₃ | CH₃ | 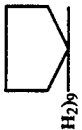 | B | 53 | 99–101 | calculated | 77.47 | 10.66 | 3.61 |
|  |  |  |  |  |  |  |  |  | found | 77.33 | 11.05 | 3.79 |
| 58 | H | CH₃ | CH₃ | CH₃ | CH₃—(CH₂)₄—CH=CH—CH₂—CH=CH—CH—(CH₂)₆—CH₃ | A | 68 | 120–122 | calculated | 78.64 | 10.61 | 3.28 |
|  |  |  |  |  |  |  |  |  | found | 78.48 | 10.76 | 3.47 |

TABLE II

Structure: benzene ring with OH (top-left), R5 (top), NH—CO—R (top-right), OH (bottom-right), R2 (bottom), R3 (bottom-left)

| Example No | R2 | R3 | R5 | R | Method | Yield (%) | Melting point (°C) | | Elemental microanalysis C % | H % | N % |
|---|---|---|---|---|---|---|---|---|---|---|---|
| 36 | CH₃ | CH₃ | CH₃ | CH₃—(CH₂)₇— | A | 77 | 174-178 | calculated | 70.32 | 9.51 | 4.56 |
| | | | | | | | | found | 70.71 | 9.56 | 4.62 |
| 37 | CH₃ | CH₃ | CH₃ | CH₃—(CH₂)₈— | A | 72 | 165-167 | calculated | 70.99 | 9.72 | 4.36 |
| | | | | | | | | found | 70.70 | 9.65 | 4.30 |
| 38 | CH₃ | CH₃ | CH₃ | CH₃—(CH₂)₉— | A | 80 | 157-159 | calculated | 71.60 | 9.91 | 4.17 |
| | | | | | | | | found | 71.66 | 9.95 | 4.34 |
| 39 | CH₃ | CH₃ | CH₃ | CH₃—(CH₂)₁₀— | A | 82 | 159-162 | calculated | 72.17 | 10.09 | 4.01 |
| | | | | | | | | found | 71.81 | 9.99 | 4.07 |
| 40 | CH₃ | CH₃ | CH₃ | CH₃—(CH₂)₁₁— | A | 78 | 155-157 | calculated | 72.69 | 10.26 | 3.85 |
| | | | | | | | | found | 73.21 | 10.23 | 3.74 |
| 41 | CH₃ | CH₃ | CH₃ | CH₃—(CH₂)₁₂— | A | 84 | 162-163 | calculated | 73.17 | 10.41 | 3.71 |
| | | | | | | | | found | 73.25 | 10.76 | 3.77 |
| 42 | CH₃ | CH₃ | CH₃ | CH₃—(CH₂)₁₄— | A | 82 | 158-160 | calculated | 74.03 | 10.69 | 3.45 |
| | | | | | | | | found | 73.84 | 10.66 | 3.41 |
| 43 | CH₃ | CH₃ | CH₃ | CH₃—(CH₂)₁₆— | A | 80 | 153-155 | calculated | 74.78 | 10.92 | 3.23 |
| | | | | | | | | found | 74.85 | 11.08 | 3.21 |
| 44 | CH₃ | CH₃ | CH₃ | CH₃—(CH₂)₁₅—C(CH₃)₂— | B | 66 | 108-110 | calculated | 75.44 | 11.13 | 3.03 |
| | | | | | | | | found | 75.27 | 11.19 | 2.97 |
| 45 | CH₃ | CH₃ | CH₃ | CH₃—(CH₂)₇—CH=CH—(CH₂)₇— (cis) | A | 76 | 155-158 | calculated | 75.13 | 10.51 | 3.24 |
| | | | | | | | | found | 75.19 | 10.49 | 3.01 |
| 46 | CH₃ | CH₃ | CH₃ | CH₃—(CH₂)₇—CH=CH—(CH₂)₇— (trans) | A | 81 | 178-180 | calculated | 75.13 | 10.51 | 3.24 |
| | | | | | | | | found | 75.55 | 10.58 | 3.18 |
| 47 | CH₃ | CH₃ | CH₃ | CH₃—(CH₂)₃—(CH₂—CH=CH)₂—(CH₂)₇— (cis, cis) | A | 71 | 162-164 | calculated | 75.48 | 10.09 | 3.26 |
| | | | | | | | | found | 75.56 | 9.94 | 3.00 |
| 48 | CH₃ | CH₃ | CH₃ | CH₃—(CH₂—CH=CH)₃—(CH₂)₇— | A | 68 | 132-134 | calculated | 75.84 | 9.66 | 3.28 |
| | | | | | | | | found | 76.17 | 9.73 | 3.28 |
| 49 | CH₃O | CH₃O | CH₃ | CH₃—(CH₂)₁₀— | A | 84 | 86-89 | calculated | 66.11 | 9.25 | 3.67 |
| | | | | | | | | found | 65.91 | 9.21 | 3.50 |
| 50 | CH₃O | CH₃O | CH₃ | CH₃—(CH₂)₈— | A | 80 | 90-92 | calculated | 64.56 | 8.84 | 3.96 |
| | | | | | | | | found | 64.58 | 8.87 | 3.98 |
| 51 | CH₃O | CH₃O | CH₃ | CH₃—(CH₂)₉— | A | 76 | 95-96 | calculated | 65.37 | 9.05 | 3.81 |
| | | | | | | | | found | 65.24 | 8.99 | 3.77 |
| 52 | CH₃O | CH₃O | CH₃ | CH₃—(CH₂)₁₁— | A | 82 | 99-102 | calculated | 66.81 | 9.43 | 3.54 |
| | | | | | | | | found | 66.81 | 8.99 | 3.38 |
| 53 | CH₃O | CH₃O | CH₃ | CH₃—(CH₂)₁₂— | A | 84 | 101-103 | calculated | 67.45 | 9.60 | 3.42 |
| | | | | | | | | found | 67.29 | 9.63 | 3.64 |
| 54 | CH₃O | CH₃O | CH₃ | CH₃—(CH₂)₁₄— | A | 81 | 107-109 | calculated | 68.62 | 9.90 | 3.20 |
| | | | | | | | | found | 68.81 | 9.90 | 3.31 |
| 55 | CH₃O | CH₃O | CH₃ | CH₃—(CH₂)₁₆— | A | 79 | 108-110 | calculated | 69.64 | 10.17 | 3.01 |
| | | | | | | | | found | 69.79 | 10.30 | 2.95 |
| 56 | CH₃O | CH₃O | CH₃ | CH₃—(CH₂)₇—CH=CH—(CH₂)₇— (cis) | A | 68 | 85-87 | calculated | 69.94 | 9.78 | 3.02 |
| | | | | | | | | found | 70.33 | 9.90 | 3.23 |

PHARMACOLOGICAL STUDY OF THE DERIVATIVES OF THE INVENTION

The inhibitory action of the compounds of the present invention was demonstrated on the one hand at the level of acyl CoA-cholesterol-acyl transferase (ACAT) of a macrophage line and, on the other hand, with respect to the oxidative modification of LDLs induced in vitro by copper sulfate.

EXAMPLE 58

Determination of ACAT

The action of the compounds of the present invention at the level of ACAT was demonstrated by means of an experimental test in vitro using a macrophage line J 774 according to the technique described by MAZIERE et al. (Atherosclerosis, 81, 151-160, 1990). This test consists in evaluating the efficacy of a product to inhibit the esterification of free intracellular cholesterol by oleic acid by determining the amount of radiolabeled cholesterol oleate formed after incubating radioactive oleyl enzyme A in the presence of a macrophage J 774 homogenate. The test products or the placebo are incubated in the presence of the macrophages for 24 hours at the concentration of $10^{-5}M$. The efficacy of these compounds is evaluated by calculating the ACAT activity of the macrophages incubated in the presence of a product relative to that of macrophages incubated in the presence of the placebo and is therefore expressed as a percentage inhibition. Under these conditions, the compounds of the invention exhibited a ACAT—inhibiting activity of the macrophages which could reach an inhibition greater than 90%.

This is the case in particular for the compounds of the following examples:

| | | | |
|---|---|---|---|
| Example 4: | 91% inhibition | Example 21: | 90% inhibition |
| Example 14: | 92% inhibition | Example 23: | 94% inhibition |
| Example 15: | 93% inhibition | Example 57: | 98% inhibition |
| Example 16: | 96% inhibition | Example 58: | 97% inhibition |
| Example 20: | 95% inhibition | | |

This activity is all the more useful as it is much more potent than that determined for two reference products: 2,4,6-trimethoxy-(9-(Z)octadecenamido)benzene (Ref. 1) and 2,4,6-trimethoxy-(2,2-dimethyldodecanamido)-benzene (Ref. 2) which, under the same conditions, exhibits only 75% inhibition.

The $IC_{50}$ of the compound described in Example 20 is equal to $2 \times 5 \times 10^{-7}M$ whereas those for the reference compounds are equal to $3 \times 10^{-6}M$ for Ref. 1 and $6 \times 10^{-6}M$ for Ref. 2.

EXAMPLE 59

Modification of the LDLs by copper sulfate

The human LDLs are incubated for 24 hours in the presence of copper sulfate ($5 \times 10^{-6}M$) with or without the test compounds (concentrations between $10^{-7}M$ and $10^{-4}M$). After incubation, the peroxidation of the LDLs is evaluated by electrophoresis on agar gel and by the formation of one of the products of lipid peroxidation: malondialdehyde (MDA) according to the technique described by PARTHASARATHY et al. (J. Clin. Invest. 77, 641-644, 1986). The activity of the compounds tested is evaluated by calculating the concentrations reducing by 50% ($IC_{50}$) the production of MDA relative to the control. The compounds of the invention exhibit-. an antioxidant activity towards human LDLs which is comparable with that of probucol taken as reference. The $IC_{50}$ values are between $3 \times 10^{-6}$ and $5 \times 10^{-6}$ for the compounds of the invention whereas the ACAT—inhibiting reference products (Ref. 1 and Ref. 2) completely lack this activity.

EXAMPLE 60

Effect of the compounds of the invention in hypercholesterolemic hamsters

Syrian golden hamsters were subjected to a 0.2% hypercholesterolemic diet for 3 weeks. They were then treated orally either by the vehicle for the compounds tested (control group), or by a reference product, or by an original product at the dose of 10 mg/kg/day for 2 weeks. At the end of the treatment, the total cholesterol was measured in the plasma.

Results

The hamsters subjected to the cholesterol enriched diet exhibited in a stable manner an increase of 100% in their level of plasma cholesterol relative to the hamsters subjected to a normal diet. The compound of Example 20 administered orally at the daily dose of 10 mg/kg exerts an excellent hypocholesterolemiant activity which normalizes the level of cholesterol in the hypercholesterolemic animals at the end of the 15 days of treatment. This activity is considerably higher than that of the reference products tested (Ref. 1 and Ref. 2) under the same conditions.

EXAMPLE 61

Pharmaceutical composition

Tablet: preparation formula for 1000 tablets containing a dose of 50 mg of active ingredient.

| | |
|---|---|
| 2,3,6-Trimethyl-4-(2-methyl-9-octadecenamido) phenol (cis isomer) | 50 g |
| Hydropropyl cellulose | 2 g |
| Wheat starch | 10 g |
| Lactose | 100 g |
| Magnesium stearate | 3 g |
| Talc | 3 g |

We claim:

1. A compound selected from those of formula (I):

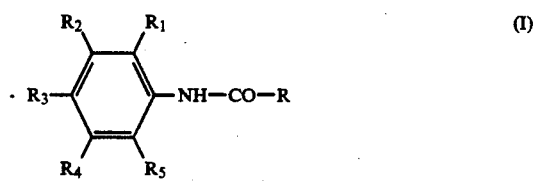

in which:
R represents linear or branched ($C_8$-$C_{21}$) alkyl, linear or branched 1-($C_8$-$C_{21}$)alkyl-($C_3$-$C_6$)cycloalk-1-yl, or linear or branched ($C_8$-$C_{21}$) alkenyl having one to three double bonds, and $R_1$ and $R_4$ represent simultaneously hydroxyl, and $R_2$, $R_3$ and $R_5$, which are identical or different, represent linear or branched ($C_1$-$C_6$) alkyl or linear or branched ($C_1$-$C_6$) alkoxy, its enantiomers, diastereoisomers and epimers, and its cis/trans isomers, as well as its addition salts with a pharmaceutically-acceptable base.

2. A compound as claimed in claim 1, selected from those wherein $R_1$ and $R_4$ represent simultaneously hydroxyl and $R_2$, $R_3$ and $R_5$ represent simultaneously, methyl, its enantiomers, diastereoisomers and epimers, and its cis/trans isomers, as well as its addition salts with a pharmaceutically acceptable base.

3. A compound as claimed in claim 1, selected from those wherein $R_1$ and $R_4$ represent simultaneously hydroxyl, $R_2$ and $R_3$ represent simultaneously methoxy, $R_5$ represents methyl, its enantiomers, diastereoisomers and epimers, and its cis/trans isomers, as well as tis addition salts with a pharmaceutically-acceptable base.

4. A method for treating an animal or human living body afflicted with dylipidemias or atherosclerosis comprising the step of administering to the living body an amount of a compound selected from those of formula (I):

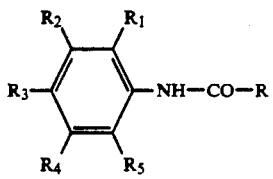

in which:
R represents linear or branched ($C_8$–$C_{21}$) alkyl, linear or branched 1-($C_8$–$C_{21}$)alkyl($C_3$–$C_6$)cycloalk-1-yl, or linear or branched ($C_8$–$C_{21}$) alkenyl having one to three double bonds,
and either
$R_3$ represents hydroxyl,
$R_1$ and $R_2$, which are different, represent hydrogen or linear or branched ($C_1$–$C_6$) alkyl, and
$R_4$ and $R_5$, which are identical or different, represent linear or branched ($C_1$–$C_6$) alkyl or linear or branched ($C_1$–$C_6$) alkoxy, or
$R_1$ and $R_4$ represent simultaneously hydroxyl, and $R_2$, $R_3$ and $R_5$, which are identical or different, represent linear or branched ($C_1$–$C_6$) alkyl or linear or branched ($C_1$–$C_6$) alkoxy,
its enantiomers, diastereoisomers and epimers, and its cis/trans isomers, as well as its addition salts with a pharmaceutically-acceptable base, which is effective for alleviation of said condition.

5. A method as claimed in claim 4, wherein $R_3$ in Formula (I) represents hydroxyl.

6. A method as claimed in claim 4, wherein $R_1$ and $R_4$ in Formula (I) simultaneously represent hydroxyl.

7. A method as claimed in claim 4, wherein In Formula (I) $R_3$ represents hydroxyl and $R_2$, $R_4$ and $R_5$ simultaneously represent methyl.

8. A method as claimed in claim 4, wherein in Formula (I) $R_3$ represents hydroxyl and $R_1$, $R_4$ and $R_5$ simultaneously represent methyl.

9. A method as claimed in claim 4, wherein in Formula (I) $R_3$ represents hydroxyl, $R_2$ represents methyl, and $R_4$ and $R_5$ simultaneously represent methoxy.

10. A method as claimed in claim 4, wherein in Formula (I) $R_1$ and $R_4$ simultaneously represent hydroxyl and $R_2$, $R_3$ and $R_5$ simultaneously represent methyl.

11. A method as claimed in claim 4, wherein in Formula (I) $R_1$ and $R_4$ simultaneously represent hydroxyl, $R_2$ and $R_3$ simultaneously represent methoxy, and $R_5$ represents methyl.

12. A method as claimed in claim 4, wherein the compound of Formula (I) is 2,3,6-trimethyl-4-(2-methylundecanamido)phenol.

13. A method as claimed in claim 4, wherein the compound of Formula (I) is 2,3,6-trimethyl-4-(2,2-dimethyl-A-amido)phenol, wherein A is undecan, dodecan, or tridecan.

14. A method as claimed in claim 4, wherein the compound of Formula (I) is 2,3,6-trimethyl-4-(2-methyl-9-octadecenamido)phenol.

15. A method as claimed in claim 4, wherein the compound of Formula (I) is 2,3,6-trimethyl-4-(9,12-octadecadienamido)phenol.

16. A method as claimed in claim 4, wherein the compound of Formula (I) is 2,3,6-trimethyl-4-(6,9,12-octadecadienamido)phenol.

17. A method as claimed in claim 4, wherein the compound of Formula (I) is 2,3,6-trimethyl-4-[(1-decyl-cyclopent-1-yl)carboxamido]phenol.

18. A method as claimed in claim 4, wherein the compound of Formula (I) is 2,3,6-trimethyl-4-(2-methyl-9,12-octadecadienamido)phenol, cis, cis isomer.

19. A pharmaceutical composition comprising as active principle an effective amount of a compound selected from those of formula (I):

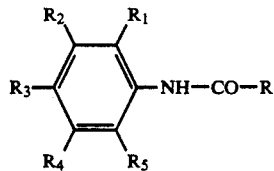

in which:
R represents linear or branch ($C_8$–$C_{21}$) alkyl, linear or branched 1-($C_8$–$C_{21}$)alkyl($C_3$–$C_6$)cycloalkyl-1-yl, or linear or branched ($C_8$–$C_{21}$) alkenyl having one to three double bonds,
and either
$R_3$ represents hydroxyl,
$R_1$ and $R_2$, which are different, represent hydrogen or linear or branched ($C_1$–$C_6$) alkyl, and
$R_4$ and $R_5$, which are identical or different, represent linear or branched ($C_1$–$C_6$) alkyl or linear or branched ($C_1$–$C_6$) alkoxy, or
$R_1$ and $R_4$ represent simultaneously hydroxyl, and $R_2$, $R_3$ and $R_5$, which are identical or different, represent linear or branched ($C_1$–$C_6$) alkyl or linear or branched ($C_1$–$C_6$) alkoxy,
its enantiomers, diastereoisomers, and epimers, and its cis/trans isomers, as well as its addition salts with a pharmaceutically-acceptable base, in combination with a pharmaceutically-acceptable excipient or vehicle.

20. A composition as claimed in claim 19, wherein $R_3$ in Formula (I) represents hydroxyl.

21. A composition as claimed in claim 19, wherein $R_1$ and $R_4$ in Formula (I) simultaneously represent hydroxyl.

22. A composition as claimed in claim 19, wherein in Formula (I) $R_3$ represents hydroxyl and $R_2$, $R_4$ and $R_5$ simultaneously represent methyl.

23. A composition as claimed in claim 19, wherein in Formula (I) $R_3$ represents hydroxyl and $R_1$, $R_4$ and $R_5$ simultaneously represent methyl.

24. A composition as claimed in claim 19, wherein in Formula (I) $R_3$ represents hydroxyl, $R_2$ represents methyl, and $R_4$ and $R_5$ simultaneously represent methoxy.

25. A composition as claimed in claim 19, wherein in Formula (I) $R_1$ and $R_4$ simultaneously represent hydroxyl and $R_2$, $R_3$ and $R_5$ simultaneously represent methyl.

26. A composition as claimed in claim 19, wherein in Formula (I) $R_1$ and $R_4$ simultaneously represent hydroxyl, $R_2$ and $R_3$ simultaneously represent methoxy, and $R_5$ represents methyl.

27. A composition as claimed in claim 19, wherein the compound of Formula (I) is 2,3,6-trimethyl-4-(2-methylundecanamido)phenol.

28. A composition as claimed in claim 19, wherein the compound of Formula (I) is 2,3,6-trimethyl-4-(2,2-demethyl-A-amido)phenol, wherein A is undecan, dodecan, or tridecan.

29. A composition as claimed in claim 19, wherein the compound of Formula (I) is 2,3,6-trimethyl-4-(2-methyl-9-octadecenenamido)phenol.

30. A composition as claimed in claim 19, wherein the compound of Formula (I) is 2,3,6-trimethyl-4-(9,12-octadecadienamido)phenol.

31. A composition as claimed in claim 19, wherein the compound of Formula (I) is 2,3,6-trimethyl-4-(6,9,12-octadecatrienamido)phenol.

32. A composition as claimed in claim 19, wherein the compound of Formula (I) is 2,3,6-trimethyl-4-](1-decylcyclopent-1-yl)carboxyamido]phenol.

33. A composition as claimed in claim 19, wherein the compound of Formula (I) is 2,3,6-trimethyl-4-(2-methyl-9,12-octadecadienamido)phenol, cis, cis isomer.

* * * * *

UNITED STATES PATENT AND TRADEMARK OFFICE
CERTIFICATE OF CORRECTION

PATENT NO. : 5,254,590
DATED : Oct. 19, 1993
INVENTOR(S) : Charles Malen, Jean-Michel Lacoste, Jean-Paul Vilaine, Albert Lenaers It is certified that error appears in the above-indentified patent and that said Letters Patent is hereby corrected as shown below:

Title page, item , [75] Inventors, last line; "Belgium" should read -- France --.
Column 2; line 4, and line 66; in each instance, underline or italicize the word "either".
Column 2, line 11; underline or italicize the word "or".
Col. 2, line 38, "1 or" should read --1 either--.
Column 2, line 68; underline "$R_3=OH$".
Column 3, line 17; underline or italicize "or".
Column 3, approximately line 50; underline "2 or".
Column 4, line 11; insert "$R_1$," at the beginning of the line.
Column 4, line 62; underline the word "either".
Column 4, line 67; underline the word "or".
Column 10, line 57; "TABLE 11." should read -- Table II. --.
Column 20, line 1; "exhibit-. an" should read --exhibit an--.
Column 21, line 3; delete the comma "," after "simultaneously".
Column 21, approximately line 11; "tis" should read --its --.
Column 22, line 16; "octadecadienamido)" should read --octadecatrienamido)--.
Column 24, line 1; "demethyl-" should read -- dimethyl --.

Signed and Sealed this

Fifth Day of July, 1994

Attest:

BRUCE LEHMAN

*Attesting Officer*            *Commissioner of Patents and Trademarks*